United States Patent
Ansari et al.

(10) Patent No.: US 8,595,206 B1
(45) Date of Patent: Nov. 26, 2013

(54) METHODS AND SYSTEMS OF CORRELATING ELECTRONIC PHARMACY DATA AND ELECTRONIC MEDICAL RECORDS

(75) Inventors: Mohsin Ovais Ansari, Highland Park, IL (US); John W. Rickord, Wheaton, IL (US)

(73) Assignee: Walgreen Co., Deerfield, IL (US)

( * ) Notice: Subject to any disclaimer, the term of this patent is extended or adjusted under 35 U.S.C. 154(b) by 34 days.

(21) Appl. No.: 13/354,581

(22) Filed: Jan. 20, 2012

(51) Int. Cl.
*G06F 17/30* (2006.01)

(52) U.S. Cl.
USPC ........... 707/706; 707/713; 707/722; 707/736; 707/758; 707/781

(58) Field of Classification Search
USPC .................................................. 707/600–899
See application file for complete search history.

(56) References Cited

U.S. PATENT DOCUMENTS

| | | |
|---|---|---|
| 2002/0035618 A1 | 3/2002 | Mendez et al. |
| 2004/0249677 A1* | 12/2004 | Datta et al. ........................ 705/3 |
| 2008/0183495 A1 | 7/2008 | Butterfield et al. |

* cited by examiner

*Primary Examiner* — Isaac M Woo
(74) *Attorney, Agent, or Firm* — Francis C. Kowalik; Marshall, Gerstein & Borun LLP; Randall G. Rueth

(57) ABSTRACT

Correlating electronic pharmacy data and electronic medical record (EMR) data may include receiving, at a correlation module and from a pharmacy computing network, a query, of a first format, for data corresponding to an EMR of a patient. The correlation module may convert the query into a second format different from the first format, and may send the converted query to another network that has access to the EMR. A response in the second format may be received, and the correlation module may convert the response into the first format and send the converted response to the pharmacy network. The correlation module may be communicatively connected with other computing networks, each corresponding to a different health care organization and each having access to a different set of EMRs. In an embodiment, the first protocol is based on an NCPDP standard, and the second protocol is based on an HL7 protocol.

22 Claims, 8 Drawing Sheets

METHODS AND SYSTEMS OF CORRELATING ELECTRONIC PHARMACY DATA AND ELECTRONIC MEDICAL RECORDS

FIELD AND BACKGROUND OF THE DISCLOSURE

1. Technical Field

The instant disclosure generally relates to correlating electronic pharmacy data and electronic medical records of patients.

2. Background

Health care costs have been increasing at a fast rate. In an attempt to reform health care, legislation in the United States that includes incentivizing payors and providers to cooperate has been passed. As such, healthcare providers are changing their approaches to providing health care to patients. Coordination of health care across multiple health care providers or health care organizations may not only decrease the cost of health care to payors, but may also improve the quality of health care to patients. Health care organizations may include pharmacy entities or enterprises that fill or provide prescription products and services, hospitals, health care data repositories, managed care organizations, physicians and/or physician groups, and other medical professionals that are licensed to prescribe medical products and medicaments to patients.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Embodiments of a system for correlating electronic pharmacy data and electronic medical records may include a correlation module, a first link that communicatively connects a correlation module and a pharmacy computer network, and a second link that communicatively connects the correlation module and a second computer network. The system may further include a database (e.g., a database that is stored on a data storage entity) whose contents may be accessible to the correlation module. The contents of the database may include data corresponding to the pharmacy network and data corresponding to the second computer network, in an embodiment. In some embodiments, the contents of the database may include data corresponding to one or more patients. The correlation module included in the system may be configured to receive, using a first protocol and via the first link, a query originated by the pharmacy network. In an embodiment, the query may be based on electronic pharmacy data that is stored in the pharmacy network. The correlation module may be further configured to determine that the query is for data included in an electronic medical record (EMR) that is accessible by the second computer network, and the correlation module may convert, based on the data corresponding to the second computer network stored in the database, the query into a second protocol used by the second computer network. The correlation module may cause the converted query to be transmitted to the second computer network via the second link.

Embodiments of a method for correlating electronic pharmacy data and electronic medical records may include receiving, at a correlation module via first link, an electronic query originated by a pharmacy computing network. The electronic query may correspond to a first protocol or format, and may be based on electronic pharmacy data stored in the pharmacy computing network. The method may further include determining, based on contents of the electronic query, that the query includes a request for data stored in an electronic medical record (EMR) corresponding to a patient, and an identity of a second computing network that has access to the EMR may be determined. The method may include converting the electronic query into a second format used by the second computing network. The conversion may be performed by the correlation module, and may be based on data corresponding to the second computing network and stored in a database that is accessible to the correlation module. Still further, the method may include causing, by the correlation module, a transmission of the converted electronic query to the second computing network via a second link.

DETAILED DESCRIPTION OF THE PREFERRED EMBODIMENTS

Figure 1:
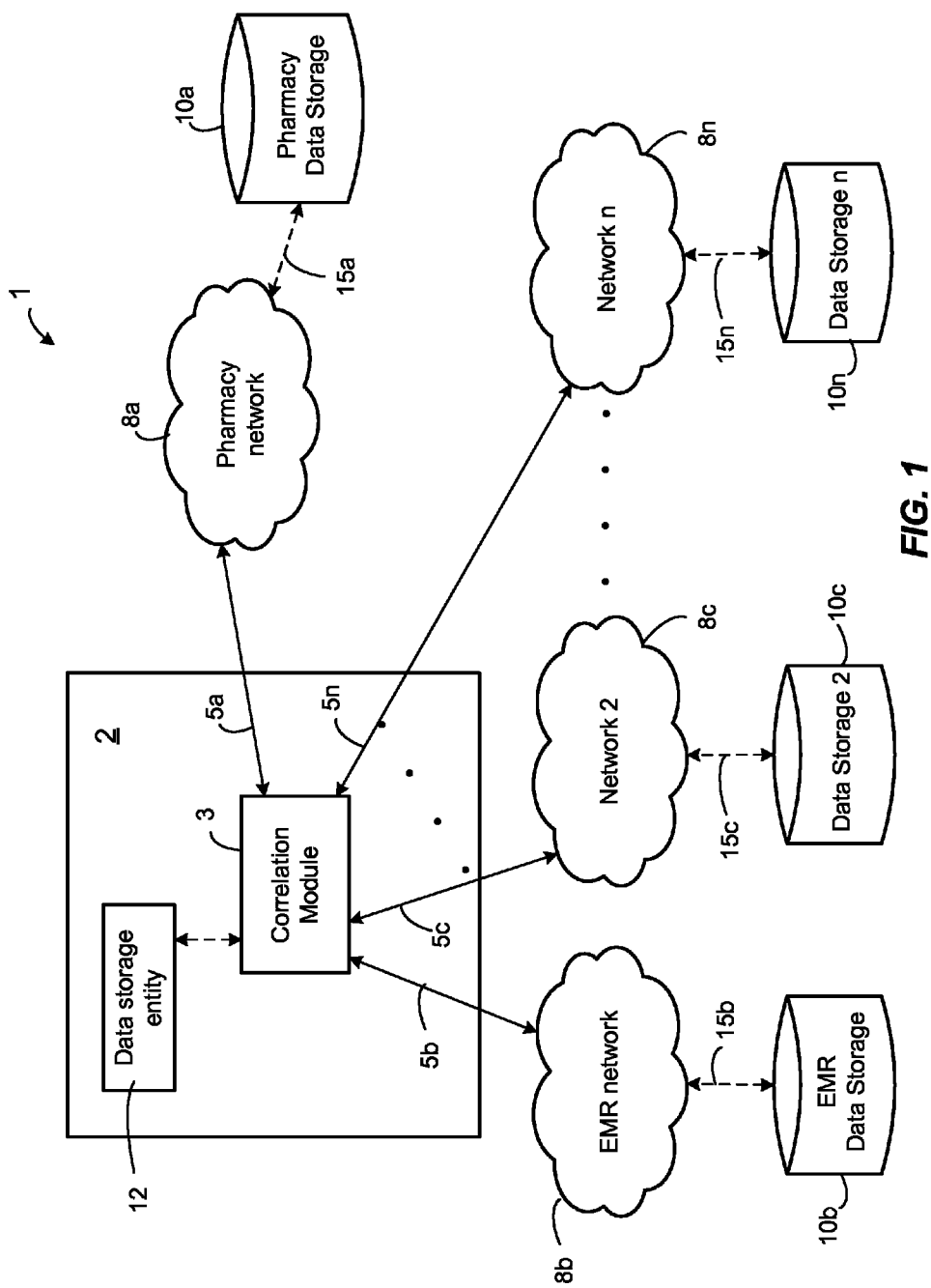
FIG. 1 is a block diagram of an example system for correlating or associating electronic pharmacy data with electronic medical records.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Any or all of the contents of the present disclosure may operate in conjunction with any or all of the contents of the disclosure of co-pending U.S. patent application Ser. No. 13/354,701 entitled "SYSTEMS AND METHODS FOR EXECUTING A PHARMACY PROGRAM THAT REQUIRES ACCESS TO AN ELECTRONIC MEDICAL RECORD" and filed concurrently herewith, the contents of which are hereby incorporated by reference in their entirety.

As used herein, the term "pharmacy enterprise" or "pharmacy company" refers to an enterprise or organization that is licensed to fill prescriptions and/or dispense prescribed pharmaceutical products such as drugs, medicaments, durable medical equipment, and the like. A pharmacy enterprise or company may provide pharmacy services such as taking prescription orders, providing oversight over prescription dispensing activities, monitoring drug therapies, counseling patients on the proper use and potential adverse events of dispensed medication, and/or other services. A pharmacy enterprise or company may be commercial or not-for-profit, and may provide or vend other products and services in addition to prescribed products and associated pharmaceutical or pharmacy services. A pharmacy enterprise or company may have one or more physical locations or facilities, including a local store front, a space within another commercial or not-for-profit enterprise (e.g., within a store, hospital, school, nursing home, etc.), a mail-order center, a call-in center, a warehouse, a distribution center, a mobile location, or an Internet or computer-order center. Generally, a pharmacy enterprise or company may employ or contract pharmacists that are licensed to practice pharmacy, pharmacy technicians, and other personnel.

Further, as used herein, the term "pharmacy enterprise computing system," "pharmacy company computing system," "pharmacy enterprise computer system," "pharmacy company computer system," "pharmacy computer system," or "pharmacy computing system" generally refers to a computing system that is owned and/or operated by a pharmacy enterprise or company to aid pharmacy enterprise personnel to fill and dispense prescribed pharmaceutical products and other products. A pharmacy enterprise computing system may include at least one computing device, and may further include at least one database, display device, and/or user interface device. The terms "pharmacy network," "pharmacy computer network," "pharmacy computing network," "pharmaceutical network," "pharmaceutical computing network," "pharmacy company network," and "pharmacy enterprise network" are interchangeably used herein to refer to a pharmacy enterprise or company computing system that includes more than one networked computing device. Typically, but not necessarily, different physical locations of a pharmacy enterprise or company may include respective computing devices, each of which is communicatively coupled to a pharmacy computing network.

A "health care organization," as used herein, refers to a health care related enterprise or health care provider. The health care organization may be for profit or not-for-profit. The health care organization may provide health care diagnostic, therapeutic, rehabilitation, and other services to patients. For example, the health care organization may provide physician care, therapy, imaging, counseling, or the like. The health care organization may provide inpatient and/or outpatient services, may include one or more physical locations or facilities. Additionally or alternatively, the health care organization may provide other health-care related services, such as providing billing management, providing health care insurance, maintaining electronic medical records, etc. Examples of health care organizations may include a hospital group, a medical practice group, an insurance group, a stand-alone imaging facility, a home-health service provider, and others. In some embodiments, a health care organization may include a pharmacy enterprise.

Further, as used herein, the term "health care organization computing system" or "health care computing system" generally refers to a computing system that is owned and/or operated by a health care organization to aid the health care organization in performing tasks required by the nature of the health care organization. For example, a health care computing system may enable a representative of the health care computing system to enter and maintain electronic medical records for a patient base. A health care computing system may include at least one computing device and may further include at least one database, display device, and/or user interface device. The terms "health care computing network," "health care organization computing network," and "health care computing system network" are interchangeably used herein to refer to a health care computing system that includes more than one networked computing device. Typically, different physical locations of a health care computing system may include respective computing devices, each of which is communicatively coupled to a health care computing system network.

FIG. 1 is a block diagram of an example system 2 for correlating or associating electronic pharmacy data with electronic medical records (EMRs). The system 2 may aid in improving the coordination of patient health care between a pharmacy enterprise and another health care organization or provider, so that the quality of health care is increased while the costs of the health care are decreased. Currently, a patient, health care organization representative or other human being (s) must be relied upon to determine the need to initiate an information exchange between a pharmacy enterprise and another health care organization or provider. Information flow between health care organizations may be stifled, and significant amounts of time and money may be required to back-track and review actions across various health care organizations. For example, when a pharmacy enterprise generates a bill corresponding to a patient's filled prescription, to properly assess charges, a representative of the pharmacy enterprise is forced to initiate an electronic or manual communication with a prescribing physician's office and the prescribing physician's office must check the patient's EMR to determine the patient's current eligibility for various government assistance programs, and finally the representative of the prescribing physician's office must report the information back to the pharmacy enterprise. This and other similar cumbersome processes may be fraught with time delays and human error, and thus may increase costs and expenses of health care, not to mention increase the chance of potentially harmful effects on patient treatment, such as when a patient declines a prescription based on an erroneous potential cost of the prescription.

On the other hand, the system 2 for correlating or associating electronic pharmacy data with electronic medical records (EMRs) may automatically coordinate information flow between a pharmaceutical provider and a health care organization to better manage a patient's health care. In particular, the system 2 may correlate electronic pharmacy data and electronic medical record data of a patient, and in particular, between a pharmacy network storing the electronic pharmacy data and a second network (e.g., a health care organization's network) storing the patient's electronic medical records. Using the system 2, pertinent and potentially time critical health care information corresponding to a patient may be easily, efficiently, accurately and more timely shared between pharmacy data and electronic medical records. As such, information flow between health care providers and other organizations is much faster and much less prone to costly errors.

Turning to FIG. 1, the system 2 for correlating or associating electronic pharmacy data with electronic medical records (EMRs) of one or more patients may include a correlation module 3 that is communicatively coupled by a first link 5a to a pharmacy network 8a. The pharmacy network 8a may be a computing network such as a private network, a public computing network, or some combination of the two. At least a portion of the pharmacy network 8a may be privately administered, managed, and/or secured by a pharmacy enterprise and may be firewalled or otherwise protected from public networks and unauthorized access. The pharmacy network 8a may be a client-server network, a peer-to-peer network, an Ethernet network, a cloud computing network, or any other known type of network in which computing devices are enabled to communicate. In some embodiments, the network 8a may include more than one different type of networking technology. The pharmacy network 8a may be included in at least a portion of a pharmacy enterprise computing system.

The pharmacy network 8a may, in turn, be communicatively coupled to a pharmacy data storage entity 10a that may store pharmaceutical or pharmacy records corresponding to patients. A pharmaceutical or pharmacy record of a patient may include information corresponding to interactions of the patient with the pharmacy enterprise, including information corresponding to prescriptions, fill dates, fill locations, refills, costs, Drug Utilization Review (DUR) results, records of pharmacist consultations, out of pocket payments, insurance or third party payments, etc. Privacy of patients' pharmaceutical or pharmacy records may be privacy protected according to local and/or federal government laws and regulations. Data other than pharmaceutical or pharmacy records may also be stored in the pharmacy storage entity 10a, in some embodiments. Although the embodiment shown in FIG. 1 illustrates the pharmacy data storage entity 10a as external to and communicatively connected to the pharmacy network 8a, in some embodiments, the pharmacy data storage entity 10a may be included within the pharmacy network 8a. The pharmacy data storage entity 10a may include one or more data storage devices of any known non-transitory, tangible storage media technology, e.g., disks, solid state devices, data banks, servers, cloud storage, etc.

The correlation module 3 may be communicatively coupled by a second link 5b to an electronic medical record (EMR) network 8b. The electronic medical record network 8b may be a computing network such as a private network, a public network, or some combination of the two. At least a portion of the electronic medical record network 8b may be privately administered by a health care organization other than the pharmacy enterprise corresponding to the pharmacy network 8a, and may be firewalled or otherwise protected from public networks and unauthorized access. The electronic medical record network 8b may be a client-server network, a peer-to-peer network, an Ethernet network, a cloud computing network, or any other known type of network in which computing devices are enabled to communicate. In some embodiments, the electronic medical record network 8b may include more than one different type of networking technology. The electronic medical record network 8b may be included in at least a portion of a health care computing system.

The EMR network or EMR computing network 8b may, in turn, be communicatively coupled to an EMR data storage entity 10b that may store electronic medical records corresponding to patients. An electronic medical record corresponding to a particular patient may be an electronic data file and may be used in lieu of or in addition to standard paper or film medical records to maintain information that pertains to health care of the particular patient. Information or data stored in an EMR may include, for example, dates of physician visits, symptoms, vital signs, consultations, diagnoses, tests and test results, courses of therapies and therapy results, etc. Privacy of patients' EMRs may be privacy protected according to local and/or federal government laws and regulations. Although the embodiment shown in FIG. 1 illustrates the EMR data storage entity 10b as being external to and communicatively connected to the EMR network 8b, in some embodiments, the EMR data storage entity 10b may be included within the EMR network 8b. The EMR data storage entity 10b may include one or more data storage devices of any known non-transitory, tangible storage media technology, e.g., disks, solid state devices, data banks, servers, cloud storage, etc.

In some embodiments, the correlation module 3 may be communicatively coupled via at least one other link 5c-5n to a respective at least one other health care network 8c-8n. Each other health care network 8c-8n may include or be communicatively coupled to respective data storage entities 10c-10n, in a manner similar to that discussed for the EMR network 8b, or in a different suitable manner. At least one of the other networks 8c-8n may be a pharmacy network different from the pharmacy network 8a, e.g., a pharmacy network corresponding to a pharmacy enterprise other than the pharmacy enterprise associated with the pharmacy network 8a.

As previously discussed, the pharmacy network 8a may be administered, managed, and/or secured by a pharmacy enterprise that is licensed or otherwise permitted to fill prescriptions, and the EMR network 8b may be administered, managed, and/or secured by a health care organization or health care provider other than the pharmacy enterprise, e.g., a hospital, a doctors' office, a medical records repository, a billing service enterprise, or the like. As such, each of the networks 8a and 8b may be a separate and independent network, and each of the networks 8a and 8b may be separately and independently managed by their respective managing or responsible enterprise or organization. Typically, each of the networks 8a and 8b may be separately secured for privacy and legal purposes by their respective enterprise or organization. For example, access to each of the networks 8a, 8b may require respective passwords, biometric identification or other means of security. In some embodiments, each of the networks 8a, 8b may reside within a respective firewall. In a similar fashion, each of the other health care networks 8c-8n may be managed by each of their respective health care organizations, such as other hospitals, medical groups, imaging centers, health insurance providers, or other health care organizations.

The correlation module 3 may be communicatively connected to a data storage entity 12. The data storage entity 12 may store, in one or more databases, data corresponding to each of the networks 8a-8n, in an embodiment. Additionally or alternatively, the data storage entity 12 may store data corresponding to one or more patients, in an embodiment, such as in the same one or more databases that store network data, and/or in different one or more databases.

Figure 2:
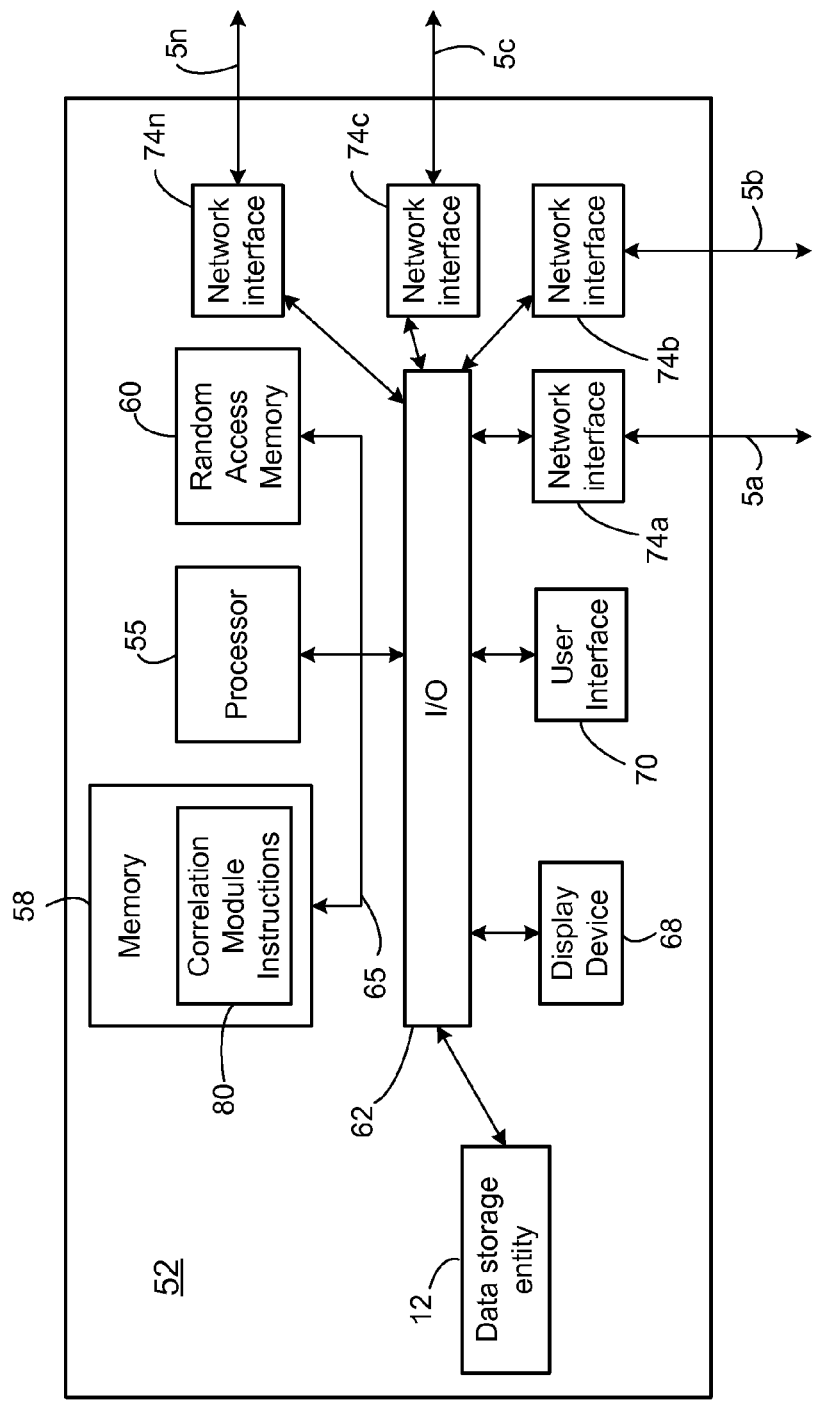
FIG. 2 illustrates an example of a simplified block diagram of a computing device that may be used in the system of FIG. 1.

In an embodiment, the correlation module 3 of the system 2 may be included on one or more computing devices or computers. FIG. 2 provides a simplified block diagram of an example of such a computing device or computer 52 to illustrate the principles of the instant disclosure. However, such principles may apply equally to other electronic devices, including, but not limited to, cellular telephones, smart phones, tablets or other wireless devices, personal digital assistants, media players, appliances, set top boxes, and automotive dashboard electronics, to name a few. Although the discussion herein refers to a single computer 52 for clarity purposes, the principles may be easily applied to more than one computer 52, such as a network of computers 52 that appears as a single logical computing device 52.

The computer 52 may include a processor 55 (may be called a controller, microcontroller or a microprocessor, in some embodiments) for executing computer-executable instructions, a program memory 58 for permanently storing data related to the computer-executable instructions, a random-access memory (RAM) 60 for temporarily storing data related to the computer-executable instructions, and an input/output (I/O) circuit 62, all of which may be interconnected via an address/data bus 65. As used herein, the terms "computer-executable instructions," "computer executable instructions," and "instructions" are used interchangeably.

In some embodiments, the computer or computing device 52 may include the data storage entity 12 illustrated in FIG. 1, and, as such, the data storage entity 12 may be locally accessible to the processor 55 and other elements of the computing device 52 via the I/O circuit 62. In some embodiments (not shown), the data storage entity 12 may be external to and separate from the computing device 52, and, as such, may be remotely accessible to the processor 55 via a network interface and a link.

It should be appreciated that although only one processor 55 is shown, the computer 52 may include multiple processors 55. Similarly, the memory of the computer 52 may include multiple RAMs (Random Access Memories) 60, multiple program memories 58, and/or multiple data storage entities 12. The RAM(s) 60, program memories 58, and/or data storage entities 12 may be implemented as one or more semiconductor memories, magnetically readable memories, optically readable memories, and/or other tangible, non-transitory computer-readable storage media, for example.

Additionally, although the I/O circuit 62 is shown as a single block, it should be appreciated that the I/O circuit 62 may include a number of different types of I/O circuits. For example, a first I/O circuit may correspond to a display device 68, and the first or a second I/O circuit may correspond to a user interface 70. The user interface 70 may be, for example, a keyboard, a mouse, a touch screen, a voice activation device, or any other known user interface device. In some embodiments, the display device 68 and the user interface 70 may be jointly incorporated in a single physical device. In some embodiments, the display device 68 and/or the user interface 70 may be omitted from the computing device 52. The computing device 52 may also include other elements common to general purpose computing devices (not shown).

The computing device or computer 52 may be operatively connected to the pharmacy network 8a via a network interface 74a and the link 5a. Similarly, the computing device 52 may be operatively connected to each of the networks 8b-8n via respective network interfaces 74b-74n and respective links 5b-5n. Each of the links 5a-5n may be as simple as a memory access function, an Ethernet connection, or the like; and/or each of the links 5a-5n may be a wired, wireless, or multi-stage connection. Many types of links are known in the art of networking and may be used in conjunction with the computing device 52.

The computing device 52 may include correlation module instructions 80 stored on a tangible, non-transitory computer-readable storage medium, such as on the memory 58 or on some other suitable memory. The correlation module instructions 80 may include one or more sets of computer-executable instructions for correlating or associating electronic pharmacy data with electronic medical records (EMRs). The instructions 80 may be executable by the processor 55 to correlate, associate, or otherwise form a correspondence between electronic pharmacy data and electronic medical records (EMRs).

Returning to FIG. 1, the pharmacy network 8a may be operatively connected to a pharmacy database or storage entity 10a via a link 15a. Similar to the link 5a, the link 15a may be any type of link known in the art. In some embodiments, the link 15a may be a link to another public or private network by which the pharmacy data storage 10a may be accessed, and the processor 5 may access the pharmacy data store 10a via the network. In some embodiments, the pharmacy data store 10a may be contained within the pharmacy network 8a itself as a networked data storage device, or the pharmacy data storage entity 10a may be contained within a memory of a computing device included in the pharmacy network 8a. In these embodiments, the link 15a may be as simple as a memory access function, an Ethernet connection, or the like. In some embodiments, the pharmacy data storage entity 10a may be a multiplicity of databases or data storage entities. Typically, but not necessarily, the pharmacy data storage entity 10a is protected from public access. The pharmacy database 10a may be included in at least a portion of a pharmacy enterprise computing system.

Similarly, one or more of the EMR and other health organization networks 8b-8n may be operatively connected to a respective database or data storage entity 10b-10n via respective links 15b-15n. Similar to the link 15a, each of the respective links 15b-15n may be any type of link known in the art. In some embodiments, the respective links 15b-15n may be links to another respective network via which the respective data storage entities 10b-10n may be accessed (e.g., the Internet, a virtual private network, or other suitable network). In these embodiments, the one or more networks 8b-8n may access its respective data store 10b-10n via the other respective network. In some embodiments, rather than being remotely accessed, at least one of the data storage entities 10b-10n may be contained within the network 8b-8n as a network data storage device or within a memory of a computing device included in the corresponding network 8b-8n for essentially local access. In some embodiments, one or more of the data storage entities 10b-10n may be a multiplicity of databases or data storage entities. Typically, but not necessarily, the data storage entities 10b-10n are protected from public access.

In some embodiments, the system 2 may be disposed between the pharmacy network 8a and the EMR network 8b, such as when the system 2 is a server or one or more computing devices that is networked to both the pharmacy network 8a and to the EMR network 8b. In some embodiments, the system 2 may be included within the pharmacy network 8a. For example, the system 2 may be included on a server or group of servers within the pharmacy network 8a, so that all computing devices corresponding to pharmacy locations within the pharmacy network 8a are serviced, for correlation purposes, by the server or group of servers on which the system 2 is included. In another example, a separate instance of the system 2 may be included in each computing device at each pharmacy location of the pharmacy computing system within the pharmacy network 8a. In some embodiments, a first instance of the system 2 may be included on each computing device of a first set of computing devices that correspond to a first set of respective pharmacy locations within the pharmacy network 8a, while a second set of computing devices that correspond to other respective pharmacy locations may be serviced, for correlation purposes, by a single server or group of servers that is included in the pharmacy network 8a and on which an instance of the system 2 is stored.

Generally, the communication format used between the correlation system 2 and the EMR network 8b and the communication format used between the correlation system 2 and the pharmacy network 8a may utilize electronic communications such as messages, file transfers, or any suitable protocol. Typically, however, the protocol used between the correlation system 2 and the EMR network 8b and the protocol used between correlation system 2 and the pharmacy network 8a may be different protocols. In some embodiments, the protocol used between correlation system 2 and the pharmacy network 8a may be, comply with, and/or correspond to at least a portion of a National Council for Prescription Drugs Programs (NCPDP) standard or format. In some embodiments, the protocol used between correlation system 2 and the pharmacy network 8a may be, comply with, and/or correspond to at least a portion of or another standard or format used by and/or within pharmacy networks other than an NCPDP standard to electronically convey electronic pharmacy data and events. In some embodiments, the protocol used between correlation system 2 and the EMR network 8b may be, comply with, and/or correspond to at least a portion of a Health Level Seven International (HL7) standard or format. In some embodiments, the protocol used between correlation system 2 and the EMR network 8b may be, comply with, and/or correspond to at least a portion of another standard or format different from the HL7 standard and used by and/or within a type of health care organization (e.g., a hospital, a medical practice, an EMR data warehouse, etc.) to electronically convey information and data. In some embodiments, the protocol used by another health organization's network (e.g., the networks 8c-8n) may be, comply with, and/or correspond to at least a portion of an HL7 standard, but may be different from the protocol used by the EMR network 8b.

FIGS. 3A-3D include example process flows used in correlating or associating electronic pharmacy data and electronic medical records between a pharmacy network 102, a correlation or association system 105, and an EMR network 108. In an embodiment, the process flows shown in FIGS. 3A-3D may operate in conjunction with embodiments of the system 2 of FIG. 1. For example, the pharmacy network 102 may be the pharmacy network 8a, the correlation or association system 105 may be the system 2, and the EMR network 108 may be the EMR network 8b of FIG. 1. In an embodiment, each of the inputs and outputs to the pharmacy network 102, the correlation or association system 105, and the EMR network 108a are processed by a computing device included respectively therein executing computer-executable instructions. For example, referring simultaneously to FIG. 2 and to FIGS. 3A-3D, at least a portion of the instructions 80 of the correlation module 3 included in the correlation system 105 may be executed at a computing device 52 to process the input and output flows illustrated in FIGS. 3A-3D.

In some embodiments, not all illustrated entities shown in FIGS. 3A-3D that send and receive messages (i.e., the pharmacy network 102, the correlation system 105, and the EMR network 108) are required. For example, instead of the EMR network 108, the process flows illustrated in FIGS. 3A-3D may operate in conjunction with some other health care organization's network (e.g., one or more of the networks 8c-8n of FIG. 1). In another example, the correlation system 105 is included in the pharmacy network 102. In fact, in some embodiments, the process flow may operate in conjunction with other suitable entities and/or systems other than those described with respect to FIG. 1. For illustrative but non-limiting purposes, however, the process flow 100 is described below in conjunction with elements of FIGS. 1 and 2.

With further respect to FIGS. 3A-3D, any communication or messaging between the correlation system 105 and the EMR network 108 or between the correlation system 105 and the pharmacy network 102 may be acknowledged and may include error scenario processing, although, for clarity purposes, such acknowledgements and error leg scenario processing communications are not shown in FIGS. 3A-3D. For example, although not shown in FIG. 3A, a reception of an EMR network registration 110 at the correlation system 105 may cause the correlation system 105 to return an acknowledgement, and if the EMR network 108 does not receive the expected acknowledgement within a defined time window, the EMR network 108 may proceed with error leg processing to resolve the situation. In another example, if the correlation system 105 receives a message or communication of an unexpected format or including unexpected data values from the pharmacy network 102, the correlation system 105 may proceed with error leg processing to resolve the situation.

Figure 3A:
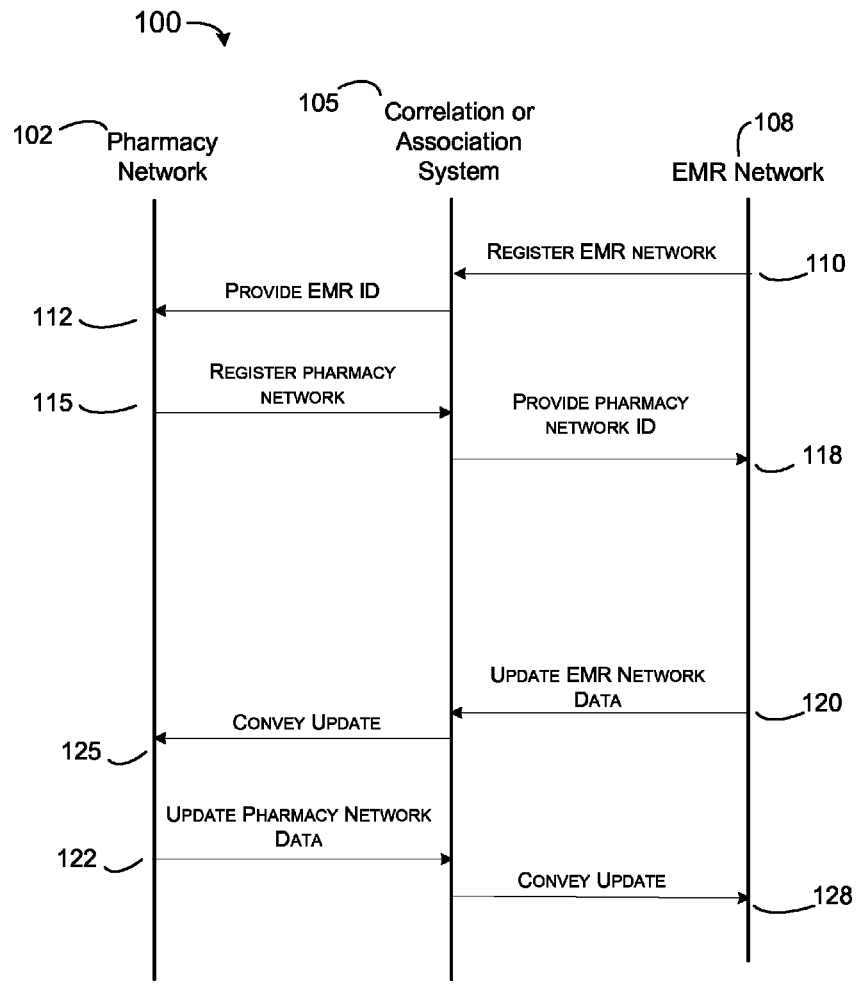
FIGS. 3A-3D illustrate example process flows that may be used in correlating or associating electronic pharmacy data with electronic medical records.

FIG. 3A illustrates an example process flow 100 for registering networks and creating network profiles at the correlation or association system 105. An EMR network or EMR computing network 108 may register 110 with the correlation or association system 105. The correlation system 105 may register the EMR network 108 by creating a profile corresponding to the EMR network 108. The EMR network profile may include at least one of: a name of the EMR network 108, a network or system identification (ID) of the EMR network 108, a name for each location or facility included in the EMR network 108 (or computing device corresponding to each location or facility), a location code, identification or ID for the each location or facility, and/or parameters corresponding to characteristics of each location. The system identification of the EMR network 108 typically, but not necessarily, may be unique within the range of system or network identifications managed by the correlation system 105. Characteristics of each location of the EMR network 108 may include, for example, an indication of whether each location is qualified for any federal or state governmental programs, such as the United States federal government's 340B Drug Pricing Program.

The EMR network profile may further include an indication of a database access mechanism, communication protocol, and/or messaging format that the EMR network 108 utilizes. For example, the EMR network profile may indicate one or more HL7 protocols or formats with which the EMR network 108 is compatible. The EMR network profile corresponding to the EMR network 108 may additionally include contact information for one or more representatives of the EMR network 108, and other administrative information. The created EMR network profile may be stored in the correlation system 105, for example, in the data storage entity 12.

In some embodiments, rather than the correlation system 105 creating the profile of the EMR network 108, the EMR network 108 may send its profile or selected portions thereof to the correlation system 105 during the registration process 110, and the correlation system 105 may store the received profile or selected portions thereof. The correlation system 105 may notify 112 the pharmacy network 102 of the assigned EMR network ID and of any other desired data corresponding to the registered EMR network 108.

In a similar manner, a pharmacy network 102 may register 115 with the correlation system 105. The correlation system 105 may register the pharmacy network 102 by creating a profile corresponding to the pharmacy network 102. The pharmacy network profile may include at least one of: a name of the pharmacy network 102, a system identification or ID of the pharmacy network 102, a name for each location or facility included in the pharmacy network 102 (or computing device corresponding to each location or facility), a location code, identification or ID for each location or facility, and/or parameters corresponding to characteristics of each location. The system identification of the pharmacy network 102 typically, but not necessarily, may be unique within the range of system or network identifications managed by the correlation system 105. Characteristics of each location included in the pharmacy network 102 may include, for example, an indication of whether each location is qualified for any federal or state governmental programs, such as the United States federal government's 340B Drug Pricing Program. The pharmacy network profile may include an indication of a database access mechanism, communication protocol, and/or messaging format that the pharmacy network 102 utilizes. For example, the pharmacy network profile may indicate one or more NCPDP standards with which the database access mechanism and/or the communication protocol utilized by the pharmacy network 102 is compatible.

The pharmacy network profile corresponding to the pharmacy network 102 may additionally include contact information for one or more representatives of the pharmacy network 102. The created pharmacy network profile may be stored in the correlation system 105, for example, in the data storage entity 12.

In some embodiments, rather than the correlation system 105 creating the profile of the pharmacy network 102, the pharmacy network 102 may send its profile or selected portions thereof to the correlation system 105 during the registration process 115, and the correlation system 105 may store the received profile or portions thereof. The correlation system 105 may notify 118 the EMR network 108 of the pharmacy network ID and of any other desired data corresponding to the pharmacy network 102.

In some embodiments, the profile of an EMR network 108 and/or the profile of the pharmacy network 102 may be independently updated 120, 122 based on respective network changes. The data included in the updates 120, 122 may reflect the respective network changes. In some embodiments, the update to the EMR network profile 120 and/or the update to the pharmacy network profile 122 may be generated in conjunction with a trigger event that occurs. For example, an update 120 may be sent to the correlation system 105 if the name of the EMR network 108 changes. In another example, when the pharmacy network 102 adds an additional pharmacy location, an update 122 may be sent to the correlation system 105. In some embodiments, at least some portion of the updated information 120, 122 may be respectively communicated 125, 128 by the correlation system 105 to the other network 102, 108.

Note that the communications 110-118 of FIG. 3A may be performed in any suitable order. For example, the pharmacy network 102 may register 115 with the correlation system 105 before the EMR network 110 registers. In some embodiments, more than one EMR or other network 108 may register (e.g., more than one of the networks 8b, 8c, 8n), so that the flows 110 and 112 are repeated for each registering EMR or other network. In some embodiments, the pharmacy network 102 may send several updates 122 while the EMR network 108 does not send any updates.

Figure 3B:
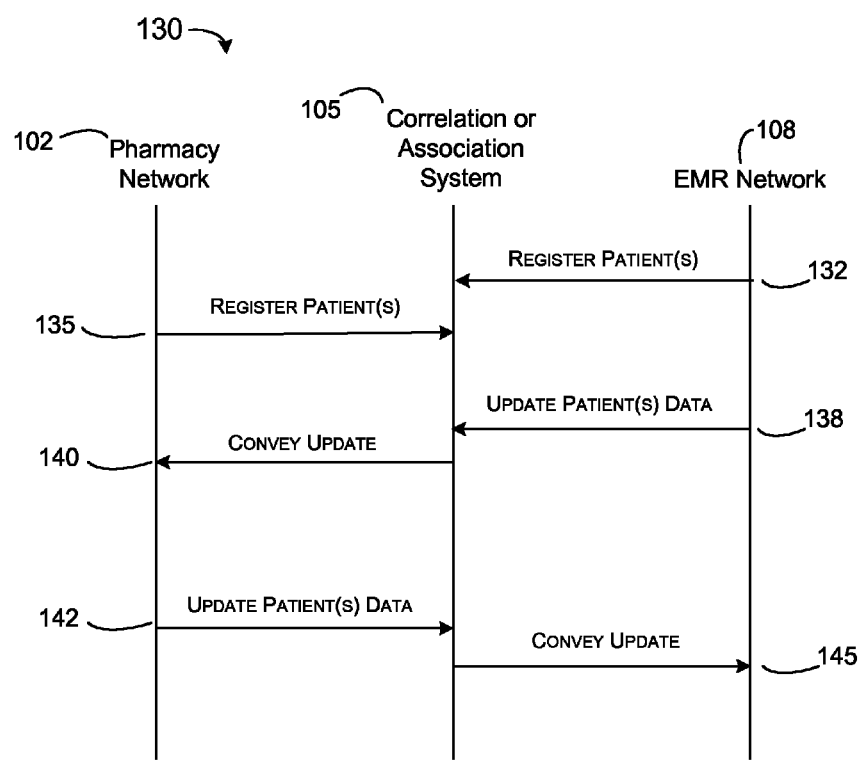

FIG. 3B illustrates an example process flow 130 for registering a patient with the correlation or association system 105. An EMR network 108 may send a patient registration 132 to the correlation or association system 105. Upon reception of the patient registration 132, the correlation system 105 may register the patient by creating a patient data file corresponding to the patient, and storing the patient data file in a data storage location that is accessible to the correlation system 105, such as the data storage entity 12.

The patient data file may include at least one of: a name of the EMR network 108 from which the patient registration 132 was received; a system identification of ID of the EMR network 108 from which the patient registration 132 was received; a patient name, address, date of birth, contact information, and other personal information; a patient medical record number or identifier; and other desired data. The contents of the patient data file may be based, at least in part, on one or more EMRs that correspond to the patient and that are stored in the EMR network 108. In an embodiment, at least a portion of the contents of one or more EMRs that correspond to the patient may be stored in the patient data file. For example, information from records of physician visits, diagnoses, orders, symptoms, and the like may be stored in the patient data file. In an embodiment, information from the one or more EMRs may be stored in the patient data file using a format utilized by the EMR network 108, such as a format that is compatible with an HL7 standard.

In some embodiments, the patient data file accessible to the correlation system 105 is a single, logical patient data file that is created for a particular patient. The logical patient data file may store aggregated data or information received from more than one registered pharmacy network, EMR network, and/or other network. In some embodiments, multiple different logical patient data files corresponding to a particular patient may be created, one for each different registered network, and these multiple patient data files corresponding to the particular patient may be linked.

In some embodiments, the patient registration 132 may be sent in conjunction with a trigger event that occurs at the EMR network 108. A trigger event may include, for example, a patient encounter. For example, a previously non-registered patient may receive health care services. As a result of received health care services, an electronic medical record corresponding to the patient may be created or updated, and the patient may be registered at the correlation system 105 after the patient encounter during which the health care services were received. In these embodiments, the patient registration 132 may also include data corresponding to patient encounter, such as the location at which the encounter occurred, the date of the encounter, parameters corresponding to characteristics of the location (such as those previously discussed with respect to the network registration 110 or other characteristics), and/or other data. In an embodiment, the patient registration 132 may include data from the EMR corresponding to the patient.

At the correlation system 105, the patient data file may be stored, for example, in the data storage entity 12. If, upon reception of the patient registration 132, the correlation system 105 determines that the patient has already been previously registered (e.g., a patient data file already exists at the correlation system 105 e.g., resulting from a previous registration received from the EMR network 108, the pharmacy network 102, or some other network), additional or updated information corresponding to the patient and included in the registration 132 may merely be added to or changed in the existing patient data file. For example, the identification of the EMR network 108 may be added to the patient data file.

In some embodiments, rather than the correlation system 105 creating the patient data file, the EMR network 108 may send a patient's data file or selected portions thereof to the correlation system 105 during the registration process of the EMR network 108 (e.g., the EMR network registration 110), and the correlation system 105 may store the received patient data file or selected portions thereof. In some embodiments, the EMR 108 may send a batch or bulk patient registration 132 to the correlation system 105, for example, when the EMR network 108 initially registers 110 with the correlation system 105, when the EMR network 108 adds a new location or group of patients, when a user request (e.g., a user request initiated at the EMR network 108, the correlation system 105 or the pharmacy network 102) for a batch registration is received, or during any desired or suitable scenario. The batch or bulk patient registration 132 may include multiple patient data files and/or data corresponding to respective multiple patients and their EMRs. In some embodiments, the bulk or batch patient registration 132 may be split across multiple transmissions from the EMR network 108 to the correlation system 105.

In a similar manner, a pharmacy network 102 may register 135 a patient with the correlation system 105. Upon reception of the registration 135, the correlation system 105 may register 135 the patient by creating a patient data file corresponding to the patient. The patient data file may include at least one of: a name of the pharmacy network 102 from which the patient registration 135 was received; a system identification or ID of the pharmacy network 102 from which the patient registration 135 was received; a patient name, address, date of birth, contact information, and other such personal information; a patient pharmaceutical or pharmacy record number or identifier; and other desired data. The patient data file may be based, at least in part, on one or more pharmaceutical or pharmacy records that correspond to the patient and that are stored in the pharmacy network 102. In an embodiment, at least a portion of the contents of one or more pharmaceutical or pharmacy records corresponding to the patient may be stored in the patient data file. For example, information corresponding to records of prescription fills and refills, consultation information, and/or the like may be stored in the patient data file. In an embodiment, the information from the one or more pharmaceutical or pharmacy records may be stored in the patient data file using a format utilized by the pharmacy network 102, such as a format that is compatible with an NCPDP standard.

In some embodiments, the patient registration 135 may be sent in conjunction with a trigger event that occurs at the pharmacy network 102 and that typically, but not necessarily, corresponds to a pharmaceutical or pharmacy record corresponding to the patient. A trigger event may include, for example, an encounter with a patient or with the patient's representative. For example, a representative of a previously non-registered patient (e.g., a parent of a minor child) may request to fill a prescription at a location within the pharmacy network 102, and a pharmaceutical or pharmacy record included in the pharmacy network 102 may be created or updated corresponding to the fill. The patient may be registered at the correlation system 105 after the pharmacy network encounter during which the prescription was filled. In these embodiments, the patient registration 135 may also include data corresponding to the encounter, such as the location at which the encounter occurred, the date of the encounter, parameters corresponding to characteristics of the location (such as those previously discussed with respect to the pharmacy network registration 115 or other characteristics), and/or other data. In an embodiment, the patient registration 135 may include data from the pharmaceutical or pharmacy record corresponding to the patient.

At the correlation system 105, the patient data file may be stored, for example, in the data storage entity 12. If, upon reception of the patient registration 135, the correlation system 105 determines that the patient has already been previously registered (e.g., a patient data file already exists, e.g., resulting from a previous registration received from the EMR network 108, the pharmacy network 102, or some other network), additional or updated information corresponding to the patient included in the patient registration 135 may merely be added to the existing patient data file at the correlation system 105. For example, the identification of the pharmacy network 102 may be added to or changed in the patient data file.

In some embodiments, rather than the correlation system 105 creating the patient data file, the pharmacy network 102 may send the patient data file or selected portions thereof to the correlation system 105 during the registration process of the pharmacy network 102 (e.g., the pharmacy network registration 115). The correlation system 105 may store the received patient data file or selected portions thereof.

In some embodiments, the pharmacy network 102 may send a batch or bulk patient registration 135 to the correlation system 105. For example, a batch or bulk patient registration 135 may be transmitted when the pharmacy network 102 initially registers with the correlation system 105, when the pharmacy network 102 adds a new location or group of patients, when a user requests a bulk registration (e.g., a user of the pharmacy network 102, the correlation system 105 or the EMR network 108 requests a batch or bulk patient registration 135 to be sent), or during any desired or suitable situation. The batch or bulk patient registration 135 may include multiple patient data files and/or data corresponding to respective multiple patients and their pharmaceutical or pharmacy records. In some embodiments, the bulk or batch patient registration 135 may be split across multiple transmissions from the pharmacy network 102 to the correlation system 105.

In some embodiments, a patient data file (or multiple patient data files) stored at the correlation system 105 may be updated 138 by the EMR network 108 based on changes made at the EMR network 108. In some embodiments, the patient update 138 may be sent from the EMR network 108 to the correlation system 105 in conjunction with a trigger event that occurs at the EMR network 108. For example, an update 138 may be sent to the correlation system 105 after a patient encounter occurs. In another example, if a patient changes his or her residence and the patient's EMR is updated with the new address, the EMR network 108 may send an update 138 to the correlation system 105 reflecting the change of address so that the correlation system may update the stored patient data file(s). In yet another example, a patient update 138 may be generated and transmitted based on a user request initiated at the EMR network 108, the correlation system 105, the pharmacy network 102, or another network. Generally, any scenario that occurs at the EMR network 108 that requires an update to data that is stored in the patient data file at the correlation system 105 may cause the EMR network 108 to generate and transmit an update 138. In some embodiments, at least some portion of the updated information 138 may be respectively communicated 140 by the correlation system 105 to the other pharmacy network 102.

In some embodiments, the EMR network 108 may send a batch or bulk patient update 138 to the correlation system 105. The batch or bulk patient update 138 may include updated data from multiple patient data files and/or updated data corresponding to respective multiple patients and their EMRs. In some embodiments, the batch or bulk patient update 138 may be split across multiple transmissions from the EMR network 108 to the correlation system 105.

In some embodiments, the content of a batch or bulk patient update 138 may be selected or filtered based on a selection parameter. The selection parameter may be indicated by a user (e.g., by an electronic user of the pharmacy network 102, of the correlation system 105, of the EMR network 108, or of some other network). The selection parameter may filter patient data to be included in the batch patient update 138 by selectable criteria such as a number of EMRs, a number of patients, a range of dates, patient program ineligibility or eligibility, a particular health care provider, or any other data or characteristic of data that may be included in or associated with a patient's data file and/or EMR. In some embodiments, more than one selection parameter may be used to filter the contents of the batch or bulk patient update 138.

In some embodiments, the batch or bulk patient update 138 may be transmitted from the EMR network 108 to the correlation system 105 at pre-determined intervals, such as hourly, daily, weekly or at any desired or suitable interval. The interval may be selectable and/or adjustable. In some embodiments, the batch or bulk patient update 138 may be sent as a result of a user request, such as a request of an electronic user initiated at the pharmacy network 102, at the correlation system 105, at the EMR network 108, or at some other network.

In some embodiments, a patient data file (or multiple patient data files) stored at the correlation system 105 may be updated 142 by the pharmacy network 102 based on changes made at the pharmacy network 102. In some embodiments, the patient update 142 may be sent from the pharmacy network 102 to the correlation system 105 in conjunction with a trigger event that occurs at the pharmacy network 102 that typically, but not necessarily, corresponds to a pharmaceutical or pharmacy record of the patient. For example, an update 142 may be sent to the correlation system 105 after a patient-related encounter occurs, such as when a parent of a minor patient picks up a filled prescription, or when a patient orders and pays for a prescription on-line. In another example, if a patient of a pharmacy network 102 changes a primary pharmacy location at which he or she receives services, the pharmacy network 102 may send an update 142 to the correlation system 105. In yet another example, a patient update 142 may be generated and transmitted based on a user request initiated at the EMR network 108, the correlation system 105, the pharmacy network 102, or another network. Generally, any scenario occurring at the pharmacy network 102 that requires an update to the patient data file at the correlation system 105 may cause the pharmacy network 102 to generate and transmit an update 142. In some embodiments, at least some portion of the updated information 142 may be communicated 145 by the correlation system 105 to the EMR network 108.

In some embodiments, the pharmacy network 102 may send a batch or bulk patient update 142 to the correlation system 105. The batch or bulk patient update 142 may include updated data from multiple patient data files and/or updated data corresponding to respective multiple patients and their pharmaceutical or pharmacy records. In some embodiments, the batch or bulk patient update 142 may be split across multiple transmissions from the pharmacy network 102 to the correlation system 105.

In some embodiments, the content of a batch or bulk patient update 142 may be selected or filtered based on a selection parameter. The selection parameter may be indicated by a user (e.g., by an electronic user of the pharmacy network 102, of the correlation system 105, of the EMR network 108, or of some other network). The selection parameter may filter patient data to be included in the batch patient update 142 by selectable criteria such as a number of pharmaceutical or pharmacy records, a number of patients, a range of dates, patient program ineligibility or eligibility status, a particular pharmacy location, or any other data or characteristic of data that may be included in or associated with a patient's data file and/or pharmaceutical or pharmacy record. In some embodiments, more than one selection parameter may be used to filter the contents of the batch or bulk patient update 142.

In some embodiments, the batch or bulk patient update 142 may be transmitted from the pharmacy network 102 to the correlation system 105 at pre-determined intervals, such as hourly, daily, weekly or at any desired or suitable interval. The interval may be selectable and/or adjustable. In some embodiments, the batch or bulk patient update 142 may be sent as a result of a user request, such as a request initiated by an electronic user of the pharmacy network 102, the correlation system 105, the EMR network 108, or some other network.

Note that the communications 132-145 of FIG. 3B may be performed in any suitable order. For example, a patient may be registered by the pharmacy network 102 before the patient is registered by the EMR network 108. In another example, a patient may be registered 135 by the pharmacy network 102 and the patient data file may be updated 142 several times by the pharmacy network 102 before the EMR network initially registers the patient 132. Other orders of the communication flows 132-145 may be possible.

Figure 3C:
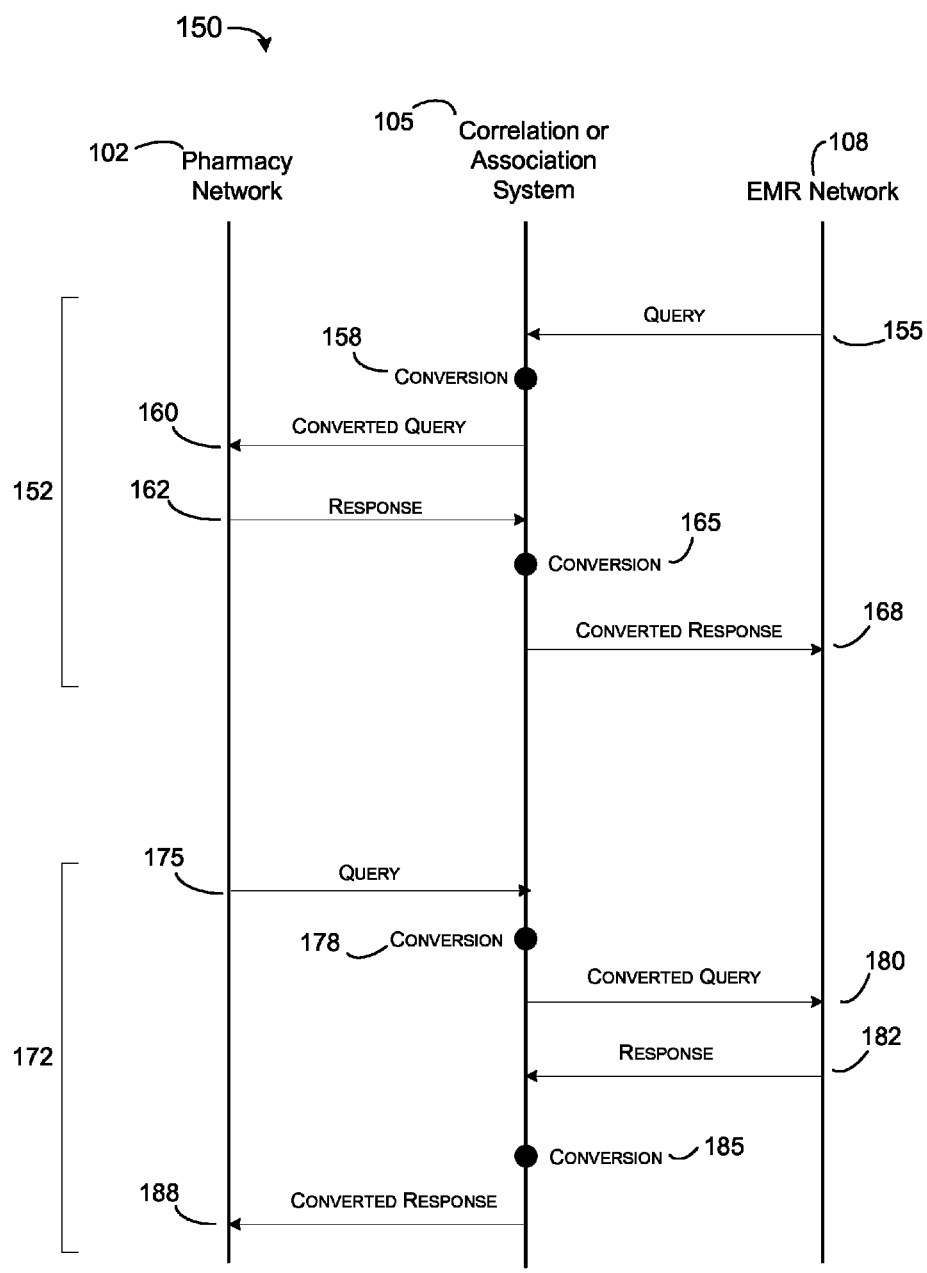

FIG. 3C illustrates an example process flow 150 for correlating pharmacy data and electronic medical records. The illustrated process flow 150 includes two sets of example communication or message exchanges 152, 172 that may occur in any order, or may both occur during an overlapping interval of time. In the first example message exchange 152, the EMR network 108 may require data that is available at the pharmacy network 102. As previously discussed, however, the EMR network 108 and the pharmacy network 102 may be each separately secured. Furthermore, the EMR network 108 and the pharmacy network 102 may each access patient data maintained therein (e.g., electronic medical records and pharmaceutical or pharmacy records, respectively) using different access mechanisms. Still further, the EMR network 108 and the pharmacy network 102 may each communicate with other networks using different protocols. For example, the EMR network 108 database access mechanism and/or the EMR network 108 communication protocol may be based, at least partially, on an HL7 format, whereas the pharmacy network 102 database access mechanism and/or the pharmacy network 102 communication protocol may be based, at least partially, on an NCPDP standard.

Accordingly, to obtain the required patient data from the pharmacy network 102, the EMR network 108 may send a query 155 to the correlation system 105. The query 155 may include a request for patient-related and/or network-related data that is available from the pharmacy network 102 but is not available from the EMR network 108. Generally, queries 155 may include one or more requests for any data that is available from a network different from the originating network (e.g., a "target" or "destination" network such as the pharmacy network 102 and/or another network 8c-8n). For example, the query 155 may include a request for patient data included in a patient's pharmaceutical or pharmacy record. In some embodiments, a query 155 may additionally or alternatively include a request for data that is specific to the destination network. For example, the query 155 may include a request for data corresponding to a particular pharmacy location included in the pharmacy network 102. The query 155 may include an indication of the target or destination network from which the desired data may be obtained, but this inclusion of the target or destination network indication is optional.

The correlation system 105 may receive the query from the originating network (e.g., the EMR network 108), and may determine the network from which the desired patient data may be obtained. For example, the correlation system 105 may determine the destination network based on the contents of the query and/or based on contents of a corresponding patient data file. Additionally or alternatively, the correlation system 105 may determine the destination network based on network information that is accessible to the correlation system 105. In an embodiment, the correlation system 105 may access one or more databases stored at the data storage entity 12 to determine the destination network.

Based on the information stored at or accessible to the correlation system 105 (e.g., stored in the data storage entity 12), the correlation system 105 may determine a format that is compatible with the destination network, and may convert 158 the query 155 into the determined format. For instance, in the example illustrated in FIG. 3C, the correlation system 105 may determine the format that is compatible with the pharmacy network 102 based on a network profile of the pharmacy network 102, and may convert 158 the query 155 into the determined format. In an embodiment, the correlation system 105 may convert 158 the query 155 by wrapping the query 155 in a wrapper that is compatible with the format compatible with the pharmacy network 102. The converted query 160 may be transmitted from the correlation system 105 to the destination network (e.g., to the pharmacy network 102).

After the destination network (e.g., the pharmacy network 102) has received the converted query 160, the destination network may generate a response 162 that includes the desired data. The response 162 may include any data that is included or stored in an EMR corresponding to the query 155, in an embodiment. The response 162 may be transmitted back to the correlation system 105, and the correlation system 105 may convert 165 the response 162 into a format that is compatible with the originating network (e.g., the EMR network 108). For instance, in the example illustrated in FIG. 3C, the correlation system 105 may determine the format that is compatible with the EMR network 108 based on a network profile of the EMR network 108 or based on data corresponding to the query 155, and may convert 165 the response 162 into the determined format. In an embodiment, the correlation system 105 converts 165 the response 162 by wrapping the response 162 in a wrapper that is compatible with the format compatible with the EMR network 108. The converted response 168 may be transmitted from the correlation system 105 to the originating network (e.g., to the EMR network 108), and the originating network may then proceed with its processing of the desired data included in the converted response 168.

With further regard to FIG. 3C, during the second example message exchange 172, the origination and the destination network roles may be reversed. In particular, the pharmacy network 102 may require data that is available at the EMR network 108. Accordingly, the pharmacy network 102 may send a query 175 to the correlation system 105. The query 175 may include a request for patient-related data and/or network-related data that is available from the EMR network 108 but is not available from the pharmacy network 102. Generally, queries 175 may include one or more requests for any patient-related data that is available on a network different from the originating network. For example, the query 175 may include a request for patient data that is included in a patient's electronic medical record. In some embodiments, a query 175 may additionally or alternatively include a request for network-related data that is specific to the destination network (e.g., data corresponding to EMR network 108). In some embodiments, the query 175 may include a request for an indication of whether or not a patient is eligible for a particular government drug program, such as the United States federal government's 340B Drug Pricing Program. For example, to determine patient eligibility for the 340B program, the query 175 may request information pertaining to patient visits to or encounters with qualified 340B program locations, and/or the query 175 may request information pertaining to time elapsed since the last patient visit to or encounter with a qualified 340B program location. The query 175 may include an indication of the target or destination network (e.g., the EMR network 108 and/or another network 8c-8n) from which the desired data may be obtained, but the inclusion of the indication of the destination network in the query 175 is optional.

The pharmacy network 102 may initiate the query when an electronic pharmacy program executing in the pharmacy network 102 requires information from the EMR network 108, such as from a particular patient's EMR. The electronic pharmacy program executing in the pharmacy network 102 may require information or data from the EMR network 108 to perform a pharmacy function such as filling a prescription; billing a prescription; counseling or dispensing advice with regard to proper or desired use of the prescription; counseling or dispensing advice with regard to possible adverse events with respect to the prescription; providing disease state management; monitoring drug therapy; and/or any other activity that is performed at a pharmacy location of the pharmacy network 102. Typically, but not necessarily, the pharmacy network 102 may initiate the query 175 based on a trigger corresponding to the pharmaceutical or pharmacy record of the particular patient. For example, the electronic pharmacy program may be a pharmacy billing program that requires an electronic check of whether or not the patient is eligible for a local, state or federal government program, such as 340B eligibility, and may initiate the query 175 while generating the bill. In another example, the electronic pharmacy program may operate in conjunction with a clinical aftercare program, a disease state management program, or a medication therapy management program in which the patient is participating, where at least a portion of the program(s) are tracked, managed, and/or executed electronically. Other examples of electronic pharmacy programs that execute at least part of a pharmacy function may be possible and may cause the pharmacy network 102 to generate or initiate a query 175 for information from another network.

The correlation system 105 may receive the query from the pharmacy network 102 and may determine the network from which the desired patient data may be obtained, i.e., the destination network. For example, the correlation system 105 may make this determination based on the contents of the query 175 and/or based on a corresponding patient data file. Additionally or alternatively, the correlation system 105 may determine the destination network based on network information that is accessible to the correlation system 105. In an embodiment, the correlation system 105 may access one or more databases at the data storage entity 12 to determine the destination network.

Based on the information stored at or accessible to the correlation system 105 (e.g., stored in the data storage entity 12), the correlation system 105 may determine a format that is compatible with the destination network, and may convert 178 the query 175 into a format that is compatible with the destination network (e.g., the EMR network 108). In FIG. 3C, for example, the correlation system 105 may convert 178 the query 175 into a format that is compatible with the EMR network 108. In an embodiment, the correlation system 105 may convert 178 the query 175 by wrapping the query 175 in a wrapper that is compatible with the format compatible with the EMR network 108. The converted query 180 may be transmitted from the correlation system 105 to the destination network (e.g., to the EMR network 108).

After the destination network (e.g., the EMR network 108) has received the converted query 180, the destination network may generate a response 182 that includes the desired data. The response 182 may include any data that is included or stored in a pharmaceutical or pharmacy record corresponding to the query 175, in an embodiment. The response 182 may be transmitted back to the correlation system 105, and the correlation system 105 may convert 185 the response 182 into a format that is compatible with the originating network (in this example, the pharmacy network 102). For instance, in the example illustrated in FIG. 3C, the correlation system 105 may determine the format that is compatible with the pharmacy network 102 based on a network profile of the pharmacy network 102 or based on data corresponding to the query 175, and may convert 185 the response 182 into the determined format. In an embodiment, the correlation system 105 converts 185 the response 182 by wrapping the response 182 in a wrapper that is compatible with the format compatible with the pharmacy network 102. The converted response 188 may be transmitted from the correlation system 105 to the originating network (e.g., to the pharmacy network 102), and the originating network may then proceed with its processing of the desired data that is included in the converted response 188.

Figure 3D:
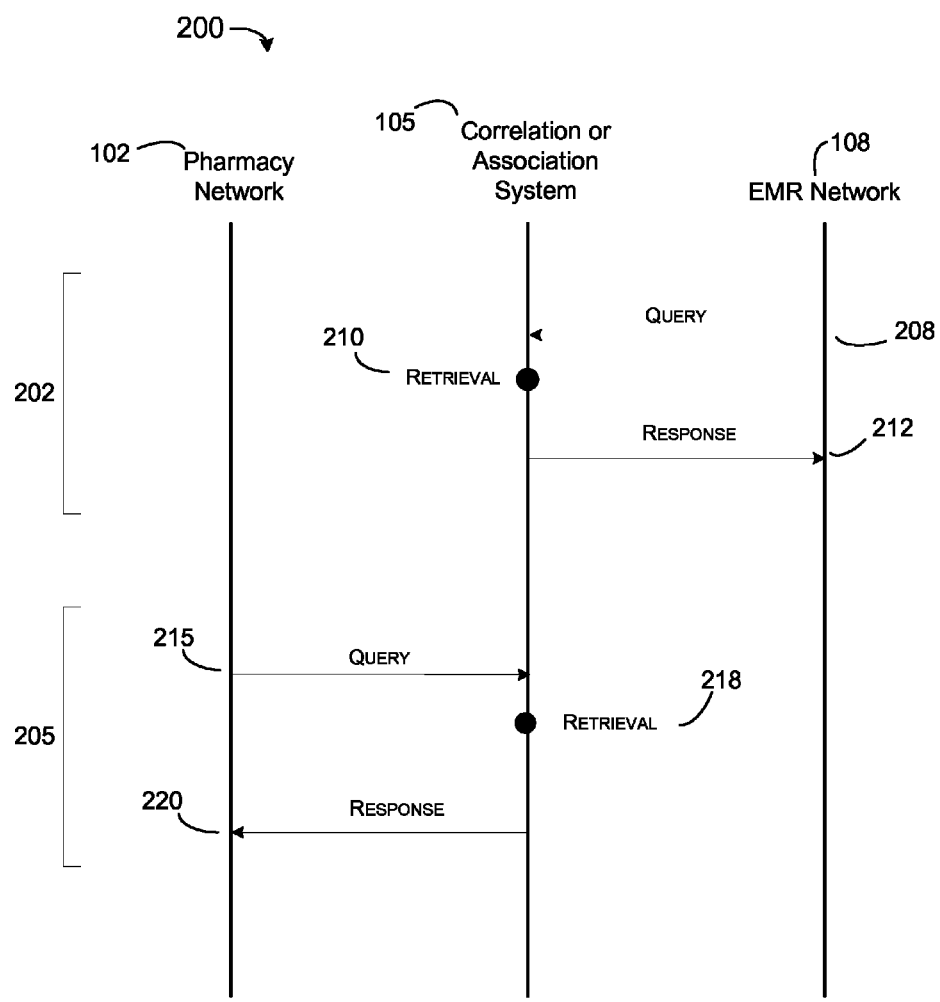

FIG. 3D illustrates an example process flow 200 for correlating pharmacy data and electronic medical records. The illustrated process flow 200 includes two sets of example communication or message exchanges 202, 205 that may occur in any order, or may both occur during an overlapping interval of time. In the first example message exchange 202, the EMR network 108 may require data that is generated by the pharmacy network 102. As previously discussed, however, the EMR network 108 and the pharmacy network 102 may be each separately secured. Furthermore, the EMR network 108 and the pharmacy network 102 may each access patient data maintained therein (e.g., electronic medical records and pharmaceutical or pharmacy records, respectively) using different access mechanisms. Still further, the EMR network 108 and the pharmacy network 102 may each communicate with other networks using different protocols. For example, the EMR network 108 database access mechanism and/or the EMR network 108 communication protocol may be based, at least partially, on an HL7 format, whereas the pharmacy network 102 database access mechanism and/ or the pharmacy network 102 communication protocol may be based, at least partially, on an NCPDP standard.

Accordingly, to obtain the required patient data generated by the pharmacy network 102, the EMR network 108 may send a query 208 to the correlation system 105. The query 208 may include a request for patient-related and/or network-related data that is generated by the pharmacy network 102. Generally, queries 208 may include one or more requests for any data that is generated by a network different from the originating network (e.g., a "target" or "destination" network such as the pharmacy network 102 and/or another network 8c-8n). For example, the query 208 may include a request for patient data included in a patient's pharmaceutical or pharmacy record. In some embodiments, a query 208 may additionally or alternatively include a request for data that is specific to the destination network. For example, the query 208 may include a request for data corresponding to a particular pharmacy location included in the pharmacy network 102. The query 208 may include an indication of the target or destination network from which the desired data may be obtained, but this inclusion of the target or destination network indication is optional.

The correlation system 105 may receive the query 208 from the originating network (e.g., the EMR network 108), and may retrieve 210 the requested information from one or more patient data files accessible to the correlation system 105 (e.g., from one or more patient data files stored in the data storage entity 12). The requested information may have been previously obtained from the pharmacy network 102 during a patient registration (e.g., message 135 of FIG. 3B) or a patient record update (e.g., message 142 of FIG. 3B), and the requested information may be stored in the one or more patient data files. In an embodiment, the information obtained from the pharmacy network 102 may be stored in the one or more patient data files in a format utilized by the pharmacy network 102 (e.g., in a format compatible with an NCPDP standard). As the query 208 may be of a format different from that utilized by the pharmacy network 102, the correlation system 105 may map one or more fields of the query 208 with respective one or more fields of the one or more patient data files.

The correlation system 105 generate a response 212, including formatting the requested information into a format that is utilized by the EMR network 108, e.g., in an HL7 compatible format. The response 212 may be transmitted from the correlation system 105 to the originating network (e.g., to the EMR network 108), and the originating network may then proceed with its processing of the desired data included in the response 212.

Accordingly, in the example process flow 200, the correlation system 105 may provide requested information or data to the originating network (e.g., the EMR network 108) by accessing locally stored information or data 210 (e.g., information or data stored in the data storage entity 12) without requiring a respective transactional communication with the network that generates or generated the requested data (e.g., the pharmacy network 102). Updates to the locally stored information or data may be initiated by the generating network (e.g., message 142 of FIG. 3B) as triggers occur. The updates initiated by the generating network, however, may be asynchronous and independent of data/information requests 208 generated by other networks (e.g., the EMR network 108). In this manner, the volume of inter-network messaging may be decreased.

With further regard to FIG. 3D, during the second example message exchange 205, the origination and the destination network roles may be reversed. In particular, the pharmacy network 102 may require data that is generated by the EMR network 108. Accordingly, the pharmacy network 102 may send a query 215 to the correlation system 105. The query 215 may include a request for patient-related data and/or network-related data that is generated by the EMR network 108 but is not available at the pharmacy network 102. Generally, queries 215 may include one or more requests for any patient-related data that is generated by or available on a network different from the originating network. For example, the query 215 may include a request for patient data that is included in a patient's electronic medical record. In some embodiments, a query 215 may additionally or alternatively include a request for network-related data that is specific to the destination network (e.g., data corresponding to EMR network 108). In an embodiment, the query 215 may include a request for an indication of whether or not a patient is eligible for a particular government drug program, such as the U.S. federal government's 340B Drug Pricing Program. For example, the query 215 may request an indication of information pertaining to patient visits to or encounters with qualified 340B program locations, and/or the query 215 may request an indication of time elapsed since the last patient visit to or encounter with a qualified 340B program location. The query 215 may include an indication of the target or destination network (e.g., the EMR network 108 and/or another network 8c-8n) from which the desired data may be obtained, but the inclusion of the indication of the destination network in the query 215 is optional.

The pharmacy network 102 may initiate the query when an electronic pharmacy program executing in the pharmacy network 102 requires information from the EMR network 108, such as from a particular patient's EMR. The electronic pharmacy program executing in the pharmacy network 102 may require information or data from the EMR network 108 to perform a pharmacy function such as filling a prescription; billing a prescription; counseling or dispensing advice with regard to proper or desired use of the prescription; counseling or dispensing advice with regard to possible adverse events with respect to the prescription; providing disease state management; monitoring drug therapy; and/or any other activity that is performed at a pharmacy location of the pharmacy network 102. Typically, but not necessarily, the pharmacy network 102 may initiate the query 215 based on a trigger corresponding to the pharmaceutical or pharmacy record of the particular patient. For example, the electronic pharmacy program may be a pharmacy billing program that requires an electronic check of whether or not the patient is eligible for a local, state or federal government program, such as 340B eligibility, and may initiate the query 215 while generating the bill. In another example, the electronic pharmacy program may operate in conjunction with a clinical aftercare program, a disease state management program, or a medication therapy management program in which the patient is participating, where at least a portion of the program(s) are tracked, managed, and/or executed electronically. Other examples of electronic pharmacy programs that execute at least part of a pharmacy function may be possible and may cause the pharmacy network 102 to generate or initiate a query 215 for information from another network.

The correlation system 105 may receive the query 215 from the originating network (e.g., the pharmacy network 102), and may retrieve 218 the requested information from one or more patient data files that are accessible to the correlation system 105 (e.g., from one or more patient data files stored in the data storage entity 12). The requested information may have been previously obtained from the EMR network 108 during a patient registration (e.g., message 132 of FIG. 3B) or a patient record update (e.g., message 138 of FIG. 3B). In an embodiment, the information obtained from the EMR network 108 may be stored in the one or more patient data files in a format utilized by the EMR network 108 (e.g., in a format compatible with an HL7 format). As the query 215 may be of a format different than that utilized by the EMR network 108, the correlation system 105 may map one or more fields of the query 215 with respective one or more fields of the one or more patient data files.

The correlation system 105 may generate a response 220 to the query 215, including formatting the requested information into a format that is known to the pharmacy network 102, e.g., in a format compatible with an NCPDP standard. The response 220 may be transmitted from the correlation system 105 to the originating network (e.g., to the pharmacy network 102), and the originating network may then proceed with its processing of the desired data included in the response 220.

Accordingly, in the example process flow 200, the correlation system 105 may provide requested information or data to the requesting network (e.g., the pharmacy network 102) by accessing locally stored information or data 218 (e.g., information or data stored in the data storage entity 12) without requiring a respective transactional communication with a network that generates the requested data (e.g., the EMR network 108). Updates to the information or data that is locally accessible to the correlation network 105 may be initiated by the generating network (e.g., message 138 of FIG. 3B) as triggers occur. The updates initiated by the generating network, however, may be asynchronous and independent of data/information requests 215 of other networks (e.g., the pharmacy network 102). In this manner, the volume of inter-network messaging may be decreased.

Any portions of the process flows 100, 130, 150 and 200 illustrated in FIGS. 3A-3D may be interspersed so that portions from different process flows occur during a same interval of time. That is, a particular process flow 100, 130, 150 and 200 need not be complete before a different process flow or another instance of the particular process flow begins. In one non-limiting example, the EMR network 108 may register 110 with the correlation system 105, and then may batch register 132 a plurality of patients. Subsequently, the pharmacy network 102 may register 115 with the correlation system 112, but prior to registering 135 any of its patients, the pharmacy network 102 may respond 162 to an EMR network query 155. In another non-limiting example, a pharmacy network 102 may register a batch of patients 135, and may update one of the patient's data 142 that was included in the batch registration 135 prior to the EMR network 108 registering 110 with the correlation system 105 at all. Of course, other examples of interleaving at least portions of one or more process flows 100, 130, 150 and 200 are possible.

Figure 4:
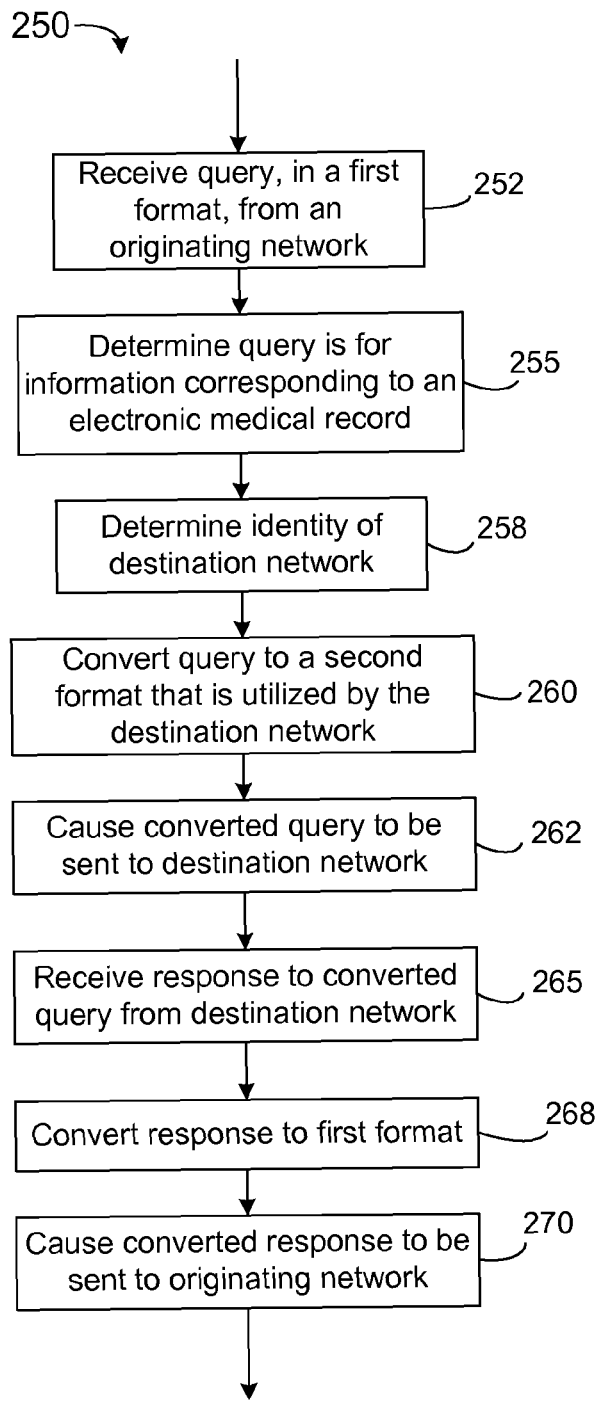
FIG. 4 is an example method for correlating or associating electronic pharmacy data with electronic medical records.

FIG. 4 is an example method 250 for correlating electronic pharmacy data and electronic medical records. Embodiments of the method 250 may operate in conjunction with the system of FIG. 1 and/or with at least a portion of any of the process flows illustrated in FIGS. 3A-3C. In an embodiment, at least a portion of the method 250 is performed by a processor of a computing device executing computer-executable instructions, for example, the processor 55 of computing device 52 executing instructions 80 as shown in FIG. 2. For illustrative and not limiting purposes, the method 250 of FIG. 4 is discussed herein with simultaneous reference to the system 2 of FIG. 1, the computing device 52 of FIG. 2, and the process flows of FIGS. 3A-3C, although the method 250 may operate in conjunction with other systems, computing devices, and/or process flows.

At a block 252, a query may be received from an originating network. The originating network may be a pharmacy network 102, an electronic medical records (EMR) network 108, or some other network 8c-8n. The query may be received, in an embodiment, at a correlation module 3 of a correlation system 105 via a link communicatively connecting the correlation module 3 with the originating network, such as via one of the links 5a, 5b, 5c, 5n.

In an embodiment, the originating network is a pharmacy network 8a, 102 including electronic pharmacy data that is stored in a data storage entity 10a that is accessible to computing entities of the pharmacy network 8a, 102. The electronic pharmacy data may include, for example, data corresponding to a patient's electronic pharmacy record.

In another embodiment, the originating network is an EMR network 8b, 108 including EMR data of one or more patients.

The EMR data may be stored in a data storage entity 10b that is accessible to computing entities of the EMR network 8b, 108.

In an embodiment, the query is an electronic query. The electronic query may have a format that is compatible with, based on, or corresponding to one or more NCPDP standards when the originating network is a pharmacy network 102. The electronic query may have a format that is compatible with, based on, or corresponding to one or more HL7 formats when the originating network is an EMR network 108.

At a block 255, a determination that the query includes a request for data stored in a network other than the origination network may be made (e.g., a request for data stored in a destination network). For example, contents of the query may be parsed and analyzed to determine that the query includes a request for data stored in a different network.

At a block 258, an identity of the destination network may be determined. In an embodiment, a particular destination network is selected or identified from a plurality of destination networks 8a-8n that is in communicative connection with the correlation module 3, where each of the plurality of destination networks 8a-8n corresponds to a different health care organization. For example, a first destination network may correspond to a hospital, a second destination network may correspond to an electronic medical record data warehouse or clearing house, a third destination network may correspond to a physical and occupational therapy practice, etc.

In an embodiment, the determined or identified destination network is a pharmacy network 102, and the requested data includes data corresponding to a pharmaceutical or pharmacy record of a patient, where the pharmaceutical or pharmacy record is stored in the pharmacy network 102. Additionally or alternatively, the requested data includes data corresponding to the pharmacy network 102 and not to any patients.

In an embodiment, the destination network is an EMR network 108, and the requested data includes data corresponding to an EMR of a patient, where the EMR is stored in the EMR network 108. Additionally or alternatively, the requested data includes data corresponding to the EMR network 108 and not to any patients.

In an embodiment, data stored in one or more databases at a data storage entity 12 that is accessible to the correlation module 3 may be utilized to determine the identity of the destination network (block 258). The one or more databases may be populated with data corresponding to each network that is communicatively connected to the correlation module 3. The data corresponding to a particular communicatively connected network may include an identification of the particular network, an indication of a format of database access utilized by the particular network, an indication of a communication format utilized by the particular network, an indication of records (e.g., patient pharmaceutical or pharmacy records, patient electronic medical records, and/or other records) that are stored or otherwise accessible to the particular network, and any other desired or suitable data. The one or more databases may be automatically at least partially populated, for example, when a particular network registers with the correlation system 105 (e.g., references 110 and/or 115), when the particular network registers patients with the correlation system 105 (e.g., references 132 and/or 135), or at other times or by other means.

In some embodiments, the query may include an indication of the destination network, and the identity of the destination network may be determined 255 by parsing the query.

At a block 260, the query may be converted into a format that is utilized by the destination network. Generally, the format utilized by the originating network is a first format, and the format utilized by the destination network is a second format different from the first format. In an embodiment, converting the query from a first format to a second format may include wrapping the query in a wrapper corresponding to or compatible with the second format. Determining the second format and the required conversion may be based on populated data that is accessible to the correlation module 3 (e.g., such as data similar to that previously described with respect to the block 258).

At a block 262, the converted query may be caused to be transmitted to the destination network. For example, the converted query may be transmitted via a link that communicatively connects the correlation module 3 and the destination network.

At a block 265, a response to the converted query may be received from the destination network at the correlation module 3. For example, the response may be formatted according to the second format, and may be received via the link that communicatively connects the correlation module 3 and the destination network.

At a block 268, the response may be converted into the first format that is utilized by the originating network. In an embodiment, the query may be converted from the second format utilized by the destination network into the first format utilized by the originating network by wrapping the response in a wrapper corresponding to or compatible with the first format. Determining the first format and the required conversion may be based on populated data that is accessible to the correlation module 3 (e.g., such as data similar to that previously described with respect to the block 258), in an embodiment. In some embodiments, an indication of the first format may have been stored upon reception of the query (block 252), and converting the response 268 may be based on the stored indication.

At a block 270, the converted response may be caused to be transmitted to the originating network. For example, the converted response may be transmitted via the link that communicatively connects the correlation module 3 and the originating network.

Multiple instances of the method 250 may execute simultaneously, may be initiated by different networks, and in some instances, may execute during an overlapping interval of time. For example, the pharmacy network 102 may initiate a query for EMR patient data, but prior to the pharmacy network 102 receiving a response to the query, the EMR network 108 may initiate a different query for pharmacy data for the same or a different patient.

Figure 5:
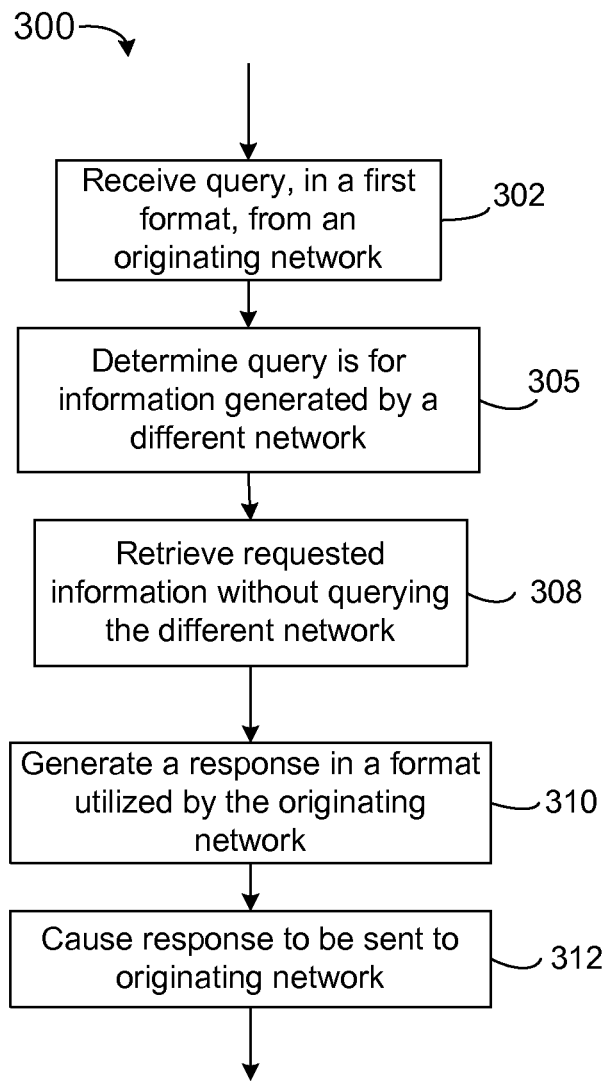
FIG. 5 is an example method for correlating or associating electronic pharmacy data with electronic medical records.

FIG. 5 is an example method 300 for correlating electronic pharmacy data and electronic medical records. Embodiments of the method 300 may operate in conjunction with the system of FIG. 1 and/or with at least a portion of any of the process flows illustrated in FIGS. 3A, 3B and 3D. In an embodiment, at least a portion of the method 300 is performed by a processor of a computing device executing computer-executable instructions, for example, the processor 55 of computing device 52 executing instructions 80 as shown in FIG. 2. For illustrative and not limiting purposes, the method 300 of FIG. 5 is discussed herein with simultaneous reference to the system 2 of FIG. 1, the computing device 52 of FIG. 2, and the process flows of FIGS. 3A, 3B and 3D, although the method 300 may operate in conjunction with other systems, computing devices, and/or process flows.

At a block 302, a query may be received from an originating network. The originating network may be a pharmacy network 102, an electronic medical records (EMR) network 108 or some other network 8c-8n. The query may be received, in an embodiment, at a correlation module 3 of a correlation system 105 via a link communicatively connecting the correlation module 3 with the originating network, such as via one of the links 5a, 5b, 5c, 5n. The query may be of a format utilized by the originating network.

In an embodiment, the originating network is a pharmacy network 8a, 102 including electronic pharmacy data that is stored in a data storage entity 10a that is accessible to computing entities of the pharmacy network 8a, 102. The electronic pharmacy data may include, for example, data corresponding to a patient's electronic pharmacy record.

In another embodiment, the originating network is an EMR network 8b, 108 including EMR data of one or more patients. The EMR data may be stored in a data storage entity 10b that is accessible to computing entities of the EMR network 8b, 108.

In an embodiment, the query is an electronic query. The electronic query may have a format that is compatible with, based on, or corresponding to one or more NCPDP standards when the originating network is a pharmacy network 102. The electronic query may have a format that is compatible with, based on, or corresponding to one or more HL7 formats when the originating network is an EMR network 108.

At a block 305, a determination that the query includes a request for data stored in or generated by a network other than the origination network may be made (e.g., a request for data stored in a different or destination network). For example, contents of the query may be parsed and analyzed to determine that the query includes a request for data stored in or generated by a different network.

In an embodiment, the determined network is a pharmacy network 102, and the requested data includes data corresponding to a pharmaceutical or pharmacy record of a patient. Additionally or alternatively, the requested data includes data corresponding to the pharmacy network 102 and not to any patients.

In an embodiment, the destination network is an EMR network 108, and the requested data includes data corresponding to an EMR of a patient. Additionally or alternatively, the requested data includes data corresponding to the EMR network 108 and not to any patients.

At a block 308, the requested information or data may be retrieved. For example, the requested information may be retrieved from one or more databases at a data storage entity 12 that are accessible to the correlation module 3. The one or more databases may have been previously and asynchronously populated by one or more networks that are communicatively connected to the correlation module 3. The populated data corresponding to a particular communicatively connected network may include an identification of the particular network, an indication of a format of database access utilized by the particular network, an indication of a communication format utilized by the particular network, an indication of records (e.g., patient pharmaceutical or pharmacy records, patient electronic medical records, and/or other records) that are stored or otherwise accessible to the particular network, at least a portion of the contents of the records generated by the particular network (e.g., the patient pharmaceutical or pharmacy records, patient electronic medical records, and/or other records), and any other desired or suitable data. The one or more databases may be automatically at least partially populated, for example, when a particular network registers with the correlation system 105 (e.g., references 110 and/or 115), when the particular network registers patients with the correlation system 105 (e.g., references 132 and/or 135), when a particular network updates patient records (e.g., references 138 and/or 142), or at other times or by other means.

At a block 310, a response to the query may be generated. The response may include the data/information that was retrieved at the block 308, and the response may be formatted into a format utilized by the originating network, e.g., the "first" format described with respect to block 302 or another suitable format. Determining the format utilized by the originating network may be based on populated data that is accessible to the correlation module 3, in an embodiment. In some embodiments, an indication of the first format may have been stored upon reception of the query (block 302), and formatting the response 310 may be based on the stored indication.

At a block 312, the generated response may be caused to be transmitted to the originating network. For example, the converted response may be transmitted via the link that communicatively connects the correlation module 3 and the originating network.

Multiple instances of the method 300 may execute simultaneously, may be initiated by different networks, and in some instances, may execute during an overlapping interval of time. In some embodiments, one or more instances of the method 300 may execute simultaneously with one or more instances of the method 250 of FIG. 4. For example, a correlation network 105 may use the method 250 to query a destination network to fulfill to a first request, while the correlation network 105 may use the method 300 to access local, previously stored data to fulfill a second request without querying the network that generates or generated the requested information.

Although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A system for correlating electronic pharmacy data and electronic medical records, comprising:
   a correlation module;
   a first link that communicatively connects the correlation module and a pharmacy computer network;
   a second link that communicatively connects the correlation module and a second computer network; and
   a database configured to store data corresponding to the second computer network,
   wherein the correlation module is configured to be executed by a processor to:
      receive, using a first protocol and via the first link, a pharmacy query originated by the pharmacy computer network, the pharmacy query being based on electronic pharmacy data corresponding to a pharmacy record corresponding to a patient, and the pharmacy record being stored in the pharmacy computer network;
      determine, based on contents of the pharmacy query, that the pharmacy query is for data included in an electronic medical record (EMR) corresponding to the patient, the EMR being stored in the second computer network;

convert, based on the data corresponding to the second computer network stored in the database, the pharmacy query into a second protocol used by the second computer network;

cause the converted pharmacy query to be transmitted to the second computer network via the second link;

receive, via the second link and using the second protocol, an EMR-based query originated by the second computer network, wherein contents of the EMR-based query are based on the EMR corresponding to the patient or are based on another EMR corresponding to another patient;

determine, based on the contents of the EMR-based query, that the EMR-based query is destined for the pharmacy computer network;

convert, based on data corresponding to the pharmacy computer network stored in the database, the EMR-based query into the first protocol used by the pharmacy computer network; and cause the converted EMR-based query to be transmitted to the pharmacy computer network via the first link.

2. The system of claim 1, wherein the correlation module is further configured to be executed by the processor to:

receive, via the second link from the second computer network and using the second protocol, a response to the converted pharmacy query;

convert, based on data corresponding to the pharmacy computer network stored in the database, the response into the first protocol; and cause the converted response to be transmitted to the pharmacy computer network via the first link.

3. The system of claim 1, wherein the first protocol is different than the second protocol and is compatible with a National Council for Prescription Drug Programs (NCPDP) standard.

4. The system of claim 1, wherein the second protocol is different than the first protocol and is compatible with a Health Level Seven International (HL7) format.

5. The system of claim 1, wherein the pharmacy query is initiated by an electronic pharmaceutical program included in the pharmacy computer network, the electronic pharmaceutical program corresponding to at least one of: an electronic check for eligibility of the patient, an electronic clinical aftercare program corresponding to the patient, a medication therapy management program corresponding to the patient, a disease state management program corresponding to the patient, or a trigger corresponding to the pharmacy record corresponding to the patient.

6. The system of claim 1, further comprising at least one other link communicatively connecting the correlation module to a respective at least one other network, and the database further storing respective data corresponding to the respective at least one other network; and wherein the correlation module is further configured to be executed by the processor to:

convert, based on the respective data corresponding to the respective at least one other network stored in the database, a subsequent pharmacy query originated by the pharmacy computer network into a protocol that is compatible with the respective at least one other network; and cause the converted subsequent pharmacy query to be transmitted to the respective at least one other network via the at least one other link.

7. The system of claim 1, wherein a conversion of the pharmacy query into the second protocol comprises a wrapper that is compatible with the second protocol and that is wrapped around the pharmacy query.

8. The system of claim 1, wherein the correlation module is included in the pharmacy computer network.

9. The system of claim 1, wherein the pharmacy computer network and the second computer network are each separately secured.

10. The system of claim 9, wherein the pharmacy computer network is secured by a pharmacy enterprise and the second computer network is secured by a health care organization other than the pharmacy enterprise.

11. A method of correlating electronic pharmacy data and electronic medical records, comprising:

receiving, at a correlation module via first link, a pharmacy electronic query that is originated by a pharmacy computing network using a first format, the pharmacy electronic query being based on electronic pharmacy data corresponding to a pharmacy record corresponding to a patient, and the pharmacy record being stored in the pharmacy computing network;

determining, by the correlation module and based on contents of the pharmacy electronic query, that the pharmacy electronic query includes a request for data stored in an electronic medical record (EMR) corresponding to the patient;

determining, by the correlation module, an identity of a second computing network that has access to the EMR corresponding to the patient;

converting, by the correlation module and based on data corresponding to the second computing network, the pharmacy electronic query into a second format used by the second computing network;

causing, by the correlation module, a transmission of the converted pharmacy electronic query to the second computing network via a second link;

receiving, at the correlation module via the second link and using the second format, an EMR-based electronic query originated by the second computing network and based on the EMR corresponding to the patient or based on another EMR corresponding to another patient;

determine, based on contents of the EMR-based electronic query, that the EMR-based electronic query is for data stored in the pharmacy record corresponding to the patient or stored in a pharmacy record corresponding to the another patient;

convert the EMR-based electronic query into the first format used by the pharmacy computing network; and cause the converted EMR-based electronic query to be transmitted to the pharmacy computing network via the first link.

12. The method of claim 11, wherein converting the pharmacy electronic query into the second format comprises wrapping the pharmacy electronic query with a wrapper that is compatible with the second format.

13. The method of claim 11, further comprising:

receiving, at the correlation module via the second link, a response to the pharmacy electronic query, the response originated by the second computing network in the second format;

converting, at the correlation module, the response into the first format; and causing, by the correlation module, the converted response to be transmitted to the pharmacy computing network via the first link.

14. The method of claim 13, wherein converting the response into the first format comprises wrapping the response with a wrapper that is compatible with the first format.

15. The method of claim 11, wherein receiving the pharmacy electronic query originated by the pharmacy computing network using the first format comprises receiving the pharmacy electronic query originated by the pharmacy computing network using a format that complies with a National Council for Prescription Drug Programs (NCPDP) standard.

16. The method of claim 11, wherein converting the pharmacy electronic query into the second format comprises converting the pharmacy electronic query into a format that is based on a Health Level Seven International (HL7) format.

17. The method of claim 11, wherein determining the identity of the second computing network comprises determining an identity of a particular computing network of a plurality of computing networks, wherein each network included in the plurality of computing networks corresponds to a different health care organization.

18. The method of claim 11, further comprising populating a database with an indication of an association between the second computing network and the second format, wherein the database is accessible to the correlation module, and wherein determining the identity of the second computing network comprises determining the second format is used by the second computing network based on the indication populated in the database.

19. The method of claim 18, wherein the indication is a first indication, and the method further comprises populating the database with a second indication of an association between the pharmacy computing network and the first format.

20. The method of claim 11, further comprising populating a database with data corresponding to the patient, the data corresponding to the patient including an indication that the EMR corresponding to the patient is stored on the second computing network, wherein the database is accessible to the correlation module, and wherein determining the identity of the second computing network comprises determining the identity of the second computing network based on the indication.

21. The method of claim 20, wherein the indication is a first indication, and the method further comprises populating the database with a second indication that the pharmacy record corresponding to the patient is stored on the pharmacy computing network.

22. A method of correlating electronic pharmacy data and electronic medical records, comprising:

receiving, at a correlation module via first link, a first electronic query that is originated by a pharmacy computing network using a first format, the first electronic query being based on electronic pharmacy data corresponding to a pharmacy record corresponding to a first patient, and the pharmacy record being stored in the pharmacy computing network;

determining, by the correlation module and based on contents of the first electronic query, that the first electronic query includes a first request for information stored in an electronic medical record (EMR) corresponding to the first patient;

determining, by the correlation module, an identity of a second computing network that has access to the EMR corresponding to the first patient;

converting, by the correlation module and based on data corresponding to the second computing network, the first electronic query into a second format used by the second computing network;

causing, by the correlation module, a transmission of the converted first electronic query to the second computing network via a second link;

receiving, at the correlation module, a second electronic query originated by the pharmacy computing network;

determining, by the correlation module, that the second electronic query includes a second request for information stored in the EMR corresponding to the first patient or for information stored in an EMR corresponding to a second patient, wherein the EMR corresponding to the first patient and the EMR corresponding to the second patient are stored at the second computing network;

retrieving, by the correlation module and without communicating with the second computing network, the information indicated by the second request;

generating, by the correlation module, a response to the second request including the retrieved information; and causing, by the correlation module, a transmission of the response to the second request to the pharmacy computing network.

* * * * *